US007563615B2

(12) United States Patent
Ponce (10) Patent No.: US 7,563,615 B2
(45) Date of Patent: Jul. 21, 2009

(54) APPARATUS AND METHOD FOR AUTOMATED MONITORING OF AIRBORNE BACTERIAL SPORES

(75) Inventor: Adrian Ponce, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 11/404,382

(22) Filed: Apr. 14, 2006

(65) Prior Publication Data

US 2007/0031916 A1 Feb. 8, 2007

Related U.S. Application Data

(60) Provisional application No. 60/671,918, filed on Apr. 15, 2005.

(51) Int. Cl.
*C12M 1/34* (2006.01)
(52) U.S. Cl. .................................................. 435/287.1
(58) Field of Classification Search ....................... None
See application file for complete search history.

(56) References Cited

U.S. PATENT DOCUMENTS

| | | | |
|---|---|---|---|
| 4,560,665 A | 12/1985 | Nakae et al. | |
| 4,943,522 A | 7/1990 | Eisinger et al. | |
| 4,965,211 A | 10/1990 | Wieder et al. | |
| 5,124,268 A | 6/1992 | Dakubu | |
| 5,792,330 A | 8/1998 | Petersen et al. | |
| 5,830,769 A | 11/1998 | Wieder et al. | |
| 5,875,960 A | 3/1999 | Rosen | 435/39 |
| 5,876,960 A | 3/1999 | Rosen | |
| 6,136,549 A | 10/2000 | Feistel | |
| 6,242,268 B1 | 6/2001 | Wieder | |
| 6,569,630 B1 | 5/2003 | Vivekananda et al. | |
| 6,599,715 B1 | 7/2003 | Vanderberg et al. | |
| 6,766,817 B2 | 7/2004 | da Silva | |
| 6,918,404 B2 | 7/2005 | Dias da Silva | |
| 7,066,586 B2 | 6/2006 | da Silva | |
| 7,306,930 B2 | 12/2007 | Ponce | 435/34 |
| 2002/0135772 A1 | 9/2002 | Bornhop et al. | |
| 2003/0064427 A1 | 4/2003 | Felkner et al. | |
| 2003/0138876 A1 | 7/2003 | Ponce et al. | |
| 2004/0014154 A1 | 1/2004 | Ponce et al. | |
| 2005/0136508 A1 | 6/2005 | Ponce | 435/39 |
| 2006/0292664 A1 | 12/2006 | Ponce | 435/34 |
| 2007/0117175 A1 | 5/2007 | Ponce | 435/29 |
| 2008/0113384 A1 | 5/2008 | Ponce | 435/34 |

FOREIGN PATENT DOCUMENTS

| | | |
|---|---|---|
| EP | 03707656 | 2/2007 |
| WO | 00/63422 | 10/2000 |
| WO | 01/83561 | 11/2001 |
| WO | 01/83561 A2 | 11/2001 |
| WO | 03/024491 | 3/2003 |
| WO | 03/024491 A2 | 3/2003 |
| WO | 03/065009 A2 | 8/2003 |
| WO | 03/067211 | 8/2003 |
| WO | WO 03/065009 | 8/2003 |
| WO | WO03/065009 A2 * | 8/2003 |

OTHER PUBLICATIONS

Slieman et al. Applied and Environmental Microbiology 2001 67(3):1274-1279.*
McBride et al. Anal. Chem. 2003 75:5293-5299.*
Belgrader, et al., "A minisonicator to rapidly disrupt bacterial spores for DNA analysis", Analytical Chemistry, 71, pp. 4232-4236 (1999).
Branda, S., et al., "Fruiting body formation by *Bacillus subtilis*," PNAS, vol. 98, No. 20, 11621-11626 (Sep. 25, 2001).
Elbanowski, et al., "The Lanthanides Probes In Investigation Of Biochemical Systems", Journal of Photochemistry and Photobiology A: Chemistry, vol. 99, pp. 85-92 (1996).
Lamture, et al., Intensity Luminescent Immunoreactive Conjugates of proteins and Dipicolinate-Based Polumeric Tb (III) Chelates, Biconjugate Chemistry, vol. 6, pp. 88-92 (1995).
Pellegrino, P., et al., "Enhanced spore detection using dipicolinate extaction techniques", Analytica Chimicha ACTA, vol. 455, No. 2, pp. 1667-177(Jan. 8, 2002).
Pellegrino, P.M., et al., "Bacterial endospore detection using terbium dipicolinate photoluminescence in the presence of chemical and biological materials", Analytical Chemistry 1998 U.S. Army Res. Lab, vol. 70, No. 9, pp. 1755 (1998).
Pierson, D., et al., "Microbial Contamination of Spacecraft", *Gravitational and Space Biology Bulletin* 14 (2) (Jun. 2001).
Scholl, P., et al., "Immunoaffinity based phosphorescent sensor platform for the detection of bacterial spores", Proc. SPIE Int Soc Opt Eng, Vaol.3913, pp. 204-214 (2000).
Seveus, et al., "Time-resolved fluorescence imaging of europheu label in immnunohistochemistry and in situ hybridization", Cytometry, 13. pp. 329-338 (1998).
U.S. Appl. No. 10/987,202, filed Nov. 12, 2004, Ponce.
Beeby, A. et al, Luminescence imaging microscopy and lifetime mapping using kinetically stable lanthanide (III) complexes, *Journal of Photochemistry and Photobiology*, B: Biology 57, pp. 83-89 (2000).
Belgrader, et al, A minisonicator to rapidly disrupt bacterial spores for DNA analysis, Analytical Chemistry, 71, pp. 4232-4236 (1999 ).
Beverly, M.B. et al., Analysis of Dipicolinic Acid in Bacterial Spores by Electron Monochromator-Mass Spectrometry, Presented at the 47th ASMS Conference on *Mass Spectrometry and Allied Topics*, Dallas, Texas, 2 pages total (Jun. 13-17, 1999).
Bio-Threat Alert (BTA™) Strips, 1 page total (Spring 2001).

(Continued)

*Primary Examiner*—Jon P Weber
*Assistant Examiner*—Bin Shen
(74) *Attorney, Agent, or Firm*—Steinfl & Bruno (57) ABSTRACT

An apparatus and method for automated monitoring of airborne bacterial spores. The apparatus is provided with an air sampler, a surface for capturing airborne spores, a thermal lysis unit to release DPA from bacterial spores, a source of lanthanide ions, and a spectrometer for excitation and detection of the characteristic fluorescence of the aromatic molecules in bacterial spores complexed with lanthanide ions. In accordance with the method: computer-programmed steps allow for automation of the apparatus for the monitoring of airborne bacterial spores.

23 Claims, 3 Drawing Sheets

OTHER PUBLICATIONS

Branda, S, et al, Fruiting body formation by *Bacillus subtilis*, *PNAS*, vol. 98, No. 20, 11621-11626 (Sep. 25, 2001).

Cable, Morgan L, et al, Bacterial Spore Detection by [Tb3+(macrocycle)(dipicolinate)] luminescence, *Beckman Institute, California Institute of Technology, Pasadena, CA* 91125, and In Situ Instruments Section, Jet Propulsion Laboratory, Pasadena, CA 91109 (2007).

Elbanowski, et al, The Lanthanides Probes in Investigation of Biochemical Systems, *Journal of Photochemistry and Photobiology A: Chemistry*, vol. 99, pp. 85-92 (1996).

Gomez-Hens, A. et al, Terbium-Sensitized Luminescence: A Selective and Versatile Analytical Approach, *Trends in Analytical Chemistry*, vol. 21, No. 2, pp. 131-141 (2002).

Hindle, A. et al, Dipicolinic Acid (DPA) Assay Revisited and Appraised for Spore Detection, *Analyst*, vol. 124, pp. 1599-1604 (1999).

Horrocks Jr., W. et al., Lanthanide Ion Luminescence Probes of the Structure of Biological Macromolecules, *American Chemical Society*, No. 14, pp. 384-392 (1981).

Koehler, T.M., *Bacillus anthracis* Genetics and Virulence Gene Regulation, *Current Topics in Microbiology & Immunology*, vol. 271, pp. 143-164, 2002.

Lamture, et al, Intensity Luminescent Immunoreactive Conjugates of proteins and oipicolinate-Based Polumeric Tb (III) Chelates, *Biconjugate Chemistry*, vol. 6, pp. 88-92 (1995).

Lester, E., et al, An Anthrax 'Smoke' Detector, *IEEE Engineering in Medicine and Biology*, pp. 38-42 (Sep./Oct. 2002).

Lutterbach, M.T.S., et al, Biofilm Formation on Brass Coupons Exposed to Cooling Water, *Brazilian Journal of Chemical Engineering*, vol. 14, No. 1 (Mar. 1997).

Lutterbach, M.T.S., et al, Biofilm Formation Monitoring in an Industrial Open Water Cooling System, *Revista de Microbiologia*, 28, pp. 106-109 (1997).

McBride, at al, Autonomous Detection of Aerosolized *Bacillus anthracis* and *Yersinia pestis*, *Anal. Chemistry*, 2003 75, 5293-5299.

Mitchell, A.C., et al, Measurement of nanosecond time-resolved fluorescence with a directly gated interline CCD camera, *Journal of Microscopy*, vol.206, Pt. 3, pp. 233-238 (Jun. 2002).

Murrell, W. G., *Chemical Composition of Spores and Spore Structures* Chapter 7 (1969).

Nicholson, W.L., et al, Resistance of *Bacillus* Endospores to Extreme Terrestrial and Extraterrestrial Environments, *Microbiology and Molecular Reviews*, vol. 64, No. 3, pp. 548-572 (Sep. 2000).

Pastuska, J, et al, Bacterial and fungal aerosol in indoor environment in Upper Silesia, Poland, *Atmospheric Environment*, 34, pp. 3833-3842 (2000).

Paratamian, S.A., Anthrax Detection, The Faster, The Better, *Microbiology 12*, Internet: http://www.college.ucla.edu/webproject/micro12/honorprojects/PartamianpOI/MicroHonorsWebPage.html pp. 1-8 (Spring 2001).

Pellegrino, P., et al, Enhanced spore detection using dipicolinate extaction techniques, *Analytica Chimicha Acta*, vol. 455, No. 2, pp. 1667-1677 (Jan. 8, 2002 ).

Pellegrino, P.M., et al, Bacterial endospore detection using terbium dipicolinate photoluminescence in the presence of chemical and biological materials, Analytical Chemistry 1998 U.S. Army Res. Lab, vol. 70, No. 9, pp. 1755 (1998).

Pierson, D., et al, Microbial Contamination of Spacecraft, *Gravitational and Space Biology Bulletin* 14 (2) (Jun. 2001).

Rode, L.J. et al, Induced Release of Dipicolinic Acid from Spores of *Bacillus megaterium*, *Journal of Bacteriology*, vol. 79, pp. 650-656 (1960).

Rose, L. , et al., Swab Materials and *Bacillus anthracis* Spore Recovery from Nonporous Surfaces, *Emerging Infectious Diseases*, vol. 10, No. 6, www.cdc.gov/eid (Jun. 2004).

Rosen, D.L., Bacterial Endospore Detection Using Photoluminescence From Terbium Dipicolinate, *Reviews Analytical Chemistry*, vol. 18, No. 1-2, pp. 1-21 (1999).

Sacks, L.E., Chemical Germination of Native and Cation-Exchanged Bacterial Spores with Trifluoperazine, *Applied* and *Environmental Biology*, vol. 56, No. 4, pp. 1185-1187 (1990).

Scholl, P. et al, Immunoaffinity based phosphorescent sensor platform for the detection of bacterial spores, Proc. SPIE Int Soc Opt Eng, vol. 3913 , pp. 204-214 (2000).

Selvin, P.R., The Renaissance of Florescence Resonance Energy Transfer, Natural *Structural Biology*, vol. 7, No. 9, pp. 730-734 (2000).

Seveus, et al., Time-resolved fluorescence imaging of europheu label in immnunohistochemistry and in situ hybridization, Cytometry, 13, pp. 329-338 (1998).

Singh, R., Microbial Diversity of Biofilms in Dental Unit Water System, *Applied and Environmental Microbiology*, pp. 3412-3420 (Jun. 2003).

Slieman et al, Role of dipocolinic acid in survival of *Bacillus subtilis* spores exposed to artificial and solar UV radiation, *Applied and Environmental Microbiology*, vol. 67, No. 3, 1274-1279, 2001.

Sorasaenee, K. et al, Cooperative Binding of Tb(III) Supramolecular Complexes with Dipicolinic Acid: Improved Sensitivity of Metal-Containing Lumophores in Biomedical Applications, *Division of Chemistry and Chemical Engineering, California Institute of Technology*, Pasadena, California, 1 page total (2003).

Uchida, L, et al, Cloning and Characterization of a Gene Whose Product Is a trans-Activator of Anthrax Toxin Synthesis, *Journal of Bacteriology*, vol. 175, No. 17 (Sep. 1993).

Vaid, A., et al, The destruction by microwave radiation of bacterial endospores and amplification of the released DNA, *Journal of Applied Microbiology*, vol. 85, pp. 115-122 (1998).

Vereb, G., et al, Temporarily and Spectrally Resolved Imaging Microscopy of Lanthanide Chelates, *Biophysical Journal*, vol. 74, pp. 2210-2222 (May 1998).

Warth, A.D., Liquid Chromatographic Determination of Dipicolinic Acid from Bacterial Spores, *Applied and Environmental Microbiology*, vol. 38, No. 6, pp. 1029-1033 (Dec. 1979).

Xiao, M., et al, An improved instrument for measuring time- resolved lanthanide emission and resonance energy transfer, *Review of Scientific Instruments*, vol. 70, No. 10 (Oct. 1999).

PCT International Search Report for PCT/US03/03036 filed on Jan. 31, 2003 in the name of California Institute of Technology.

PCT International Search Report for PCT/US2006/022988 filed on Jun. 13, 2006 in the name of California Institute of Technology.

PCT Written Opinion for PCT/US2006/022988 filed on Jun. 13, 2006 in the name of California Institute of Technology, et al.

A. J. Alvarez, M. Khanna, G A. Toranzos, and G Stotzky, "Amplification of DNA bound on clay minerals," *Molecular Ecology*, vol. 7, pp. 775-778, 1998.

R. I. Amann, W. Ludwig, and K. H. Schleifer, "Phylogenetic Identification and in-Situ Detection of Individual Microbial-Cells without Cultivation," *Microbiological Reviews*, vol. 59,pp. 143-169, 1995.

Balzani V, Decola L, Prodi L, Scandola F: Photochemistry of Supramolecular Species. *Pure Appl Chem 1990*, 62:1457-1466.

Balzani V: Supramolecular Photochemistry. *Pure Appl Chem* 1990, 62:1099-1102.

D. L. Balkwill, F. R. Leach, J. T. Wilson, J. F. McNabb, and D. C. White, "Equivalence of Microbial Biomass Measures Based on Membrane Lipid and Cell-Wall Components, Adenosine-Triphosphate, and Direct Counts in Subsurface Aquifer Sediments," *Microbial Ecology*, vol. 16, pp. 73-84, 1988.

P. Belgrader. W. Benett, D. Hadley. I. Richards, P. Stratlon, R. Mariella and F. P. Milanovich, "Infectious disease—PCR detection of bacteria in seven minutes." *Science*, vol. 284. pp. 449-450, 1999.

P. Belgrader, C.I. Elkin. S.B, Brown. S.N. Nasarabadi, R.G. Langlois, F.P. Milanovich, B.W. Colston, and G.D. Marshall. "A reusable flow-through polymerase chain reaction instrument for the continuous monitoring of infectious biological agents," *Analyt. Chem* . vol. 75, pp. 3446-3450, 2003.

M. Carl. R. Hawkins, N. Coulson. I. Lowe. D.L. Robertson. W.M. Nelson, R.W. Titball and J.N. Woody. "Detection of spores of *Bacillus•anthracis* using the polymerase chain-reaction," *J. Infectious Diseases*, vol. 165, pp. 1145-1148. 1992.

A. Castro and R.T. Okinaka, "Ultrasensitive, direct detection of a specific DNA sequence of *Bacillus anthracis* in solution," *Analyst*. vol. 125. pp. 9-11, 1999.

B. D. Church and H. Halvorson, "Dependence of the Heat Resistance of Bacterial Endospores on Their Dipicolinic acid Content," *Nature*, vol. 183, pp. 124-125, 1959.

R. Connally, D. Veal, and J. Piper, "High resolution detection of fluorescently labeled microorganisms in environmental samples using time-resolved fluorescence microscopy," *Fems Microbiology Ecology*, vol. 41, pp. 239-245, 2002.

Enserink M: Anthrax: Biodefence Hampered by Inadequate Tests. *Science* 2001, 294:1266-1267.

J.W. Ezzell. T.G. Absbire. S.F. Little, B.C. Lidgerding. and C. Brown, "Identification of *Bacillus-anthracis* by using monoclonal-antibody to cell-wall antibody to cell-wall galacttose-N-acetylglucosamine polysaccharide," *J. Clin. Microbiol*, vol. 28, pp. 223-231, 1990.

Grenthe I: Stability Relationships among the Rare Earth Dipicolinates. *Journal of the American Chemical Society* 1961, 83: 360-364.

W.D. Griffiths and G.A.L. Decosemo. "The assessment of bioaerosols-A critical- review," *J. Aerosol Sci.*. vol. 25, pp. 1425-1458. 1994.

W.D. Griffiths, I.W. Stewan. S.J. Futter, S.L. Upton, and D. Mark, "The development of sampling methods for the assessment of indoor bioaerosols," *J. Aerosol ScL*, vol. 28. pp. 437-457, 1997.

I. Henderson. C.J. Duggleby, and P.C.B. Turnbull. "Differentiation of *Bacillus-anthracis* from other *Bacillus-cereus* group bacteria with the Pcr," *Inl. J. Systematic Bacteriol.*, vol. 44. pp. 99-105. 1994.

J. Ho, "Future of biological aerosol detection," *Analyrica Chimica Acta*, vol. 457, pp. 125-148, 2002.

P.M. Holland. R.D. Abramson, R. Watson. and D.H. Gelfand, "Detection of specific polymerase chain-reaction product by utilizing the 5'-3' exonuclease activity of thermus-aquaticus DNA-polymerase," in *Proc. Nat. Acad. Sci. USA*, vol. 88. 1991. pp. 7276-7280.

G. Horneck, H. Bucker, and G. Reitz, "Long-Term Survival of Bacterial-Spores in-Space," *Life Sciences and Space Research*), vol. 14, pp. 41-45, 1994.

W. D. Horrocks Jr., "Lanthanide Ion Luminescence in Coordination Chemistry and Biochemistry," in *Progress in Inorganic Chemistry*, vol. 31. New York: Wiley, 1984, pp. 1.

Hunnicutt, D. W., M. J. Kempf, and M. J. McBride. 2002. Mutations in *Flavobacteriumjohnsoniae gldF* and *gldG* disrupt gliding motility and interfere with membrane localization of GldA. *J. Bacteriol*. 184: 2370-2378.

T.V. Inglesby, D.A. Henderson, J.G. Bartlett, M.S. Ascher. E. Eitzen, A.M. Friedlander, J. Hauer. J. McDade, M.T. OSterholm, T. O-Toole, G. Parker, T.M.mPerl, P.K. Russell, and K. Tonat, "Anthrax as a biological weapon—Medical and public health management," *JAMA*, vol. 281, pp. 1735-1745. 1999.

K. Ito, K. Nakagawa, S. Murakami, H. Arakawa, and M. Maeda, "Highly sensitive simultaneous Bioluminescent measurement of acetate kinase and pyruvate phosphate dikinase activities using a firefly luciferase-luciferin reaction and its application to a tandem Bioluminescent enzyme immunoassay," *Analytical Sciences*, vol. 19, pp. 105-109, 2003.

F.W. Janssen, A.J. Lund. and L.E. Anderson, "Colorimetric assay for dipicolinic acid In bacterial spores," *Science*, vol. 127. pp. 26-27, 1958.

M. Johns. L. Harrington, R.W. Titball, and D.L. Leslie. "Improved methods for the detection of *Bacillus-anthracls* spores by the polymerase chain-reaction," *Lett. Appl. Microbiol*. vol. 18, pp. 236-238.1994.

J. G Jones, "Effect of Environmental-Factors on Estimated Viable and Total Populations of Planktonic Bacteria in Lakes and Experimental Enclosures," *Freshwater Biology*, vol. 7, pp. 67-91, 1977.

Kempf. M. J. and M. J. McBride. 2000. Transposon insertions in the *Flavobacterium johnsoniae ftsX* gene disrupt gliding motility and cell division. J. *Bacteriol*. 182: 1671-1679.

J. Knight, "US postal service puts anthrax detectors to the test," *Nature*, vol. 417, pp. 579-579, 2002.

L. J. Kricka, "Chemiluminescence and bioluminescence," *Analytical Chemistry*, vol. 71, pp. 305R-308R, 1999.

D.B. Lacy and R.J. Collier. "Structure and function of anthrax toxin," in *Anthrax, Current Topics In Microbiology and Immunology*, vol. 271, pp. 61-85, 2002.

D. Lawrence, S. Heitefuss, and H.S.H. Seifert, "Differentiation of *Bacillusanthracis* from *Bacillus-cereus* by gas-chromatographic whole-cell fatty-acid analysis," *J. Clin. Microbiol*. vol. 29, pp. 1S08-1512, 1991.

Lehn JM: Supramolecular Chemistry-Scope and Perspectives Molecules, Supermolecules, and Molecular Devices. *Angewandte Chemie-International Edition in English* 1988, 27:89-112.

Lester E et al: "A second-generation anthrax smoke detector" IEEE Engineering in Medicine and Biology Magazine, IEEE Service Center, Piscataway, NJ, US, vol. 23, No. 1, Jan. 2004, pp. 130-135, XP001201545 ISSN: 0739-5175 the whole document.

N.A. Logan, J.A. Carman, I. Melling, and R.C.W. Berkeley. "Identification of *Bacillus-antbracis* by api tesIS," *J. Medical Microbial*. vol. 20, pp. 75-85, 1985.

A. Lundin, "Use of firefly luciferase in ATP-related assays of biomass, enzymes, and metabolites," *Bioluminescence and Chemiluminescence*, Pt C, vol. 305, pp. 346-370,2000.

G Manfredi, A. Spinazzola, N. Checcarelli, and A. Naini, "Assay of mitochondrial ATP synthesis in animal cells," *Methods in Cell Biology*. vol. 65, vol. 65, pp. 133-145, 2001.

McBride, M. J. and M. J. Kempf. 1996. Development of techniques for the genetic manipulation of the gliding bacterium *Cytophaga johnsonae*. J. *Bacteriol*. 178: 583-590.

A. C. Mitchell, J. E. Wall, J. G. Murray, and C.G. Morgan, "Direct modulation of the effective sensitivity of a CCD detector: a new approach to time-resolved fluorescence imaging," *Journal of Microscopy—Oxford*, vol. 206, pp. 225-232, 2002.

M. M. Moeseneder, J. M. Arrieta, G Muyzer, C. Winter, and G J. Herndl, "Optimization of terminal-restriction fragment length polymorphism analysis for complex marine bacterioplankton communities and comparison with denaturing gradient gel electrophoresis," *Applied and Environmental Microbiology*, vol. 65, pp. 3518-3525, 1999.

C. G Morgan and A. C. Mitchell, "Fluorescence lifetime imaging: An emerging technique in fluorescence microscopy," *Chromosome Research*, vol. 4, pp. 261-263, 1996.

W. Nicholson and P. Setlow; "Sporulation, germination and outgrowth," *Molecular biology methods for bacillus*, S. Cutting, Ed. Sussex, England: John Wiley and Sons, 1990, 391-450).

M. Paidhungat, B. Setlow, A. Driks, and P. Setlow, "Characterization of spores of *Bacillus subtilis* which lack dipicolinic acid," *Journal ofBacteriology*, vol. 182, pp. 5505-5512, 2000.

G. Patra, P. Sylvestre, V. Ramisse, I. Therasse, and Il. Guesdon. "Isolation of a specific chromosomic DNA sequence of *Bacillus anthracis* and its possible use in diagnosis," *Fems Immunol. Medical Microblol.*, vol. 15. pp. 223-231. 1996.

A.P. Phillips and K.L. Martin. "Evaluation of a microfluorometer in Immunofluorescence assays of individual spores of *Bacillus-anthracis* and *Bacillus-cereus*," *J.ImnwntJlogical MetiuJdJ*, vol. 49, pp. 271-282. 1982.

A.P. Phillips, K.L. Martin, N.L. Cross, R.G. Drake, "Evaluation of immunoradiometric and Elisa versions of a microtitre plate assay for *Bacillusanlhracis* spores," *J. Immunological Merhod1*, vol. 70, pp. 75-81, 1984.

A.P. Phillips and K.L. Martin. "Quantitative immunofluorescenoe studies of the serology of *Bacillus-anthracis* spores," *Appl. Environmenral Microbiol.*, vol. 46, pp. 1430-1432, 1983.

V. Ramisse, G. Patra. H. Garrigue. J.L. Guesdon, and M. Mock, "Identification and characterization of *Bacillus anthracis* by multiplex PCR analysis of sequences on plasmids pXO1 and pX02 and chromosomal DNA," Ferns *Microbiol. Lett*. vol. 145, pp. 9-16, 1996.

C. Redmond, M.J. Pearce, R.T. Manchee, and B.P. Berdal, "Deadly relic of the great war," *Nature*. vol. 393. pp. 747-748. 1998.

Rosen DL, Sharpless C, McGown LB: Bacterial Spore Detection and Determination by Use of Terbium Dipicolinate Photoluminescence. *Anal Chem* 1997, 69: 1082-1085.

Rosen DL: Wavelength Pair Selection for Bacterial Endospore Detection by Use of Terbium Dipicolinate Photoluminescence. *Appl Optics* 1998, 37: 805-807.

Sabbatini N, Guardigli M, Lehn J M: Luminescent Lanthanide Complexes as Photochemical Supramolecular Devices. *Coord Chem Rev 1993*, vol. 123:201-228.

M. Schena, D. Shalon, R. W. Davis, and P. O. Brown, "Quantitative Monitoring of Gene-Expression Patterns with a Complementary-DNA Microarray," *Science*, vol. 270, pp. 467470, 1995.

Sinha S: *Systematics and the Properties of the Lanthanides*. Edited by Sinha S: NATO ASI Series 109; 1983.

P. Sneath, "Longevity of micro-organisms," *Nature*, vol. 195, pp. 643-646, 1962.

P.J. Stopa, "The flow cytometry of *Bacillus anthracis* spores revisited," *Cytometry*, vol. 41, pp. 237-244, 2000.

B.N. Strizhkov, A.L. Drobyshev, V.M. Mikhailovlch, and A.D. Mirzabekov, "PCR amplification on a microarray of gel-immobilized oligonucleotides: Deteclion of bacterial toxin- and drug-resistant genes and their mutations," *Biotechnique.*, vol. 29. pp. 844-??? 2000.

V. Torsvik, I. Goksoyr, and F. L. Daae, "High Diversity in DNA of Soil Bacteria," *Applied and Environmental Microbiology*, vol. 56, pp. 782-787, 1990.

P.C.B. Turnbull. "Definitive identification of *Bacillus anthsacis*-A review," *J. Applied Microbiol*, vol. 87. pp. 237-240. 1999.

M. Varughese, A.V. Teixeira, S.H. Liu. and S.H. Leppla. "Identification of a receptor•binding region within domain 4 of the protective antigen component of anthrax *toxin.*" *Infection and Immunity*, vol. 67, pp. 1860-1865, 1999.

Venkateswaran, K., M. Kempf. F. Chen, M. Satomi, W. Nicholson, and R. Kern. 2003. *Bacillus nealsonii* sp. nov. isolated from a spacecraft assembly facility, whose spores are gamma-radiation resistant. *Int. J. Syst. Evol. Microbiol*. 53: 165-172.

G Vereb, E. Jares-Erijman, P. R. Selvin, and T. M. Jovin, "Temporally and spectrally resolved imaging microscopy oflanthanide chelates," *Biophysical Journal*, vol. 74, pp. 2210-2222, 1998.

R. H. Vreeland, W. D. Rosenzweig, and D. W. Powers, "Isolation of a 250 million-year old halotolerant bacterium from a primary salt crystal," *Nature*, vol. 407, pp. 897-900,2000.

D. C. White, W. M. Davis, J. S. Nickels, J. D. King, and R. J. Bobbie, "Determination of the Sedimentary Microbial Biomass by Extractable Lipid Phosphate," *Oecologia*, vol. 40, pp. 51-62, 1979.

A. Ponce, "Live/Dead Bacterial Spore Assay Using DPA-Triggered Tb Luminescence," *Photonics Tech Briefs*, vol. 27, No. 3, p. 7a, Mar. 2003.

A. Ponce, "Species Specific Bacterial Spore Detection Using Lateral-Flow Immunoassay . . . " *Photonics Tech Briefs*, vol. 27, No. 3. pp. 6a-7a, Mar. 2003.

R. L. Mancinelli and M. Klovstad, "Martian soil and UV radiation: microbial viability assessment on spacecraft surfaces," Planetary and Space Science, vol. 48, pp. 1093-1097, 2000.

Cable, M.L., et al., "Bacterial Spore Detection by [$Tb^{3+}$(macrocycle)(dipicolinate)] Luminecsence" J of American Chemical Society, 2007:129 (6) :1474-1475.

Beeby, A., et al. , "Luminescence imaging microscopy and lifetime mapping using kinetically stable lanthanide (III) complexes", *Journal of Photochemistry and Photobiology*, B: Biology 57, pp. 83-89 (2000).

Beverly, M.B., et al., "Analysis of Dipicolinic Acid in Bacterial Spores by Electron Monochromator-Mass Spectrometry," *Presented at the 47th ASMS Conference on Mass Spectrometry and Allied Topics*, Dallas, Texas, 2 pages total (Jun. 13-17, 1999).

"Bio-Threat Alert (BTA™) Strips," 1 page total (Spring 2001).

Branda, S., et al., "Fruiting body formation by *Bacillus subtilis,*" *PNAS*, vol. 98, No. 20, 11621-11626 (Sep. 25, 2001).

Gómez-Hens, A., et al., "Terbium-Sensitized Luminescence: A Selective and Versatile Analytical Approach," *Trends in Analytical Chemistry*, vol. 21, No. 2, pp. 131-141 (2002).

Hindle, A., et al., "Dipicolinic Acid (DPA) Assay Revisited and Appraised for Spore Detection," *Analyst*, vol. 124, pp. 1599-1604 (1999).

Horrocks Jr., W., et al., "Lanthanide Ion Luminescence Probes of the Structure of Biological Macromolecules", *American Chemical Society*, No. 14, pp. 384-392 (1981).

Koehler, T.M., "*Bacillus anthracis* Genetics and Virulence Gene Regulation," *Current Topics in Microbiology & Immunology*, vol. 271, pp. 143-164, 2002.

Lester, E., et al., "An Anthrax "Smoke" Detector", *IEEE Engineering in Medicine and Biology*, pp. 38-42 (Sep./Oct. 2002).

Lutterbach, M.T.S., et al., "Biofilm Formation on Brass Coupons Exposed to Cooling Water", *Brazilian Journal of Chemical Engineering*, vol. 14, No. 1 (Mar. 1997).

Lutterbach, M.T.S., et al., "Biofilm Formation Monitoring in an Industrial Open Water Cooling System," *Revista de Microbiologia*, 28, pp. 106-109 (1997).

Mitchell, A.C., et al., "Measurement of nanosecond time-resolved fluorescence with a directly gated interline CCD camera", Journal of Microscopy, vol. 206, Pt. 3, pp. 233-238 (Jun. 2002).

Nicholson, W.L., et al., "Resistance of *Bacillus* Endospores to Extreme Terrestrial and Extraterrestrial Environments", *Microbiology and Molecular Reviews*, vol. 64, No. 3, pp. 548-572 (Sep. 2000).

Pastuska, J., et al., "Bacterial and fungal aerosol in indoor environment in Upper Silesia, Poland," *Atmospheric Environment*, 34, pp. 3833-3842 (2000).

Paratamian, S.A., "Anthrax Detection, The Faster, The Better," *Microbiology* 12, Internet: <http://www.college.ucla.edu/webproject/micro12/honorprojects/Partamianp01/MicroHonorsWebPage.html> pp. 1-8 (Spring 2001).

Pierson, D., et al., "Microbial Contamination of Spacecraft", *Gravitational and Space Biology Bulletin* 14 (2) (Jun. 2001).

Rode, et al., "Induced Release of Dipicolinic Acid From Spores of *Bacillus megaterium*", *Journal of Bacteriology*, vol. 79, pp. 650-656 (1960).

Rose, L., et al., "Swab Materials and *Bacillus anthracis* Spore Recovery from Nonporous Surfaces", *Emerging Infectious Diseases*, vol. 10, No. 6, www.cdc.gov/eid (Jun. 2004).

Rosen, D.L., "Bacterial Endospore Detection Using Photoluminescence From Terbium Dipicolinate," *Reviews Analytical Chemistry*, vol. 18, No. 1-2, pp. 1-21 (1999).

Sacks, L.E., "Chemical Germination of Native and Cation-Exchanged Bacterial Spores with Trifluoperazine," *Applied and Environmental Biology*, vol. 56, No. 4, pp. 1185-1187 (1990).

Abstract of Scholl, P., et al., "Immunoaffinity Based Phosphorescent Sensor Platform for the Detection of Bacterial Spores," *Proceedings of the SPIE*, vol. 3913, 1 page total (2002).

Selvin, P.R., "The Renaissance of Flourescense Resonance Energy Transfer", *Natural Structural Biology*, vol. 7, No. 9, pp. 730-734 (2000).

Singh, R., "Microbial Diversity of Biofilms in Dental Unit Water System", *Applied and Environmental Microbiology*, pp. 3412-3420 (Jun. 2003).

Sorasaenee, K., et al., "Cooperative Binding of Tb(III) Supramolecular Complexes with Dipicolinic Acid: Improved Sensitivity of Metal-Contaning Lumophores in Biomedical Applications," *Division of Chemistry and Chemical Engineering, California Institute of Technology*, Pasadena, California, 1 page total (2003).

Uchida, I., et al., "Cloning and Characterization of a Gene Whose Product Is a trans-Activator of Anthrax Toxin Synthesis", *Journal of Bacteriology*, vol. 175, No. 17 (Sep. 1993).

Vaid, A., et al., "The destruction by microwave radiation of bacterial endospores and amplification of the released DNA", *Journal of Applied Microbiology*, vol. 85, pp. 115-122 (1998).

Vereb, G., et al., "Temporarily and Spectrally Resolved Imaging Microscopy of Lanthanide Chelates", Biophysical Journal, vol. 74, pp. 2210-2222 (May 1998).

Warth, A.D., "Liquid Chromatographic Determination of Dipicolinic Acid from Bacterial Spores," *Applied and Environmental Microbiology*, vol. 38, No. 6, pp. 1029-1033 (Dec. 1979).

Xiao, M., et al., "An improved instrument for measuring time-resolved lanthanide emission and resonance energy transfer", *Review of Scientific Instruments*, vol. 70, No. 10 (Oct. 1999).

\* cited by examiner

APPARATUS AND METHOD FOR AUTOMATED MONITORING OF AIRBORNE BACTERIAL SPORES

CROSS REFERENCE TO RELATED APPLICATIONS

This application claims priority to U.S. Provisional Ser. No. 60/671,918 for "Automated Monitoring of Airborne Bacterial Spores" filed on Apr. 15, 2005, incorporated herein by reference in its entirety. This application may also be related to U.S. Ser. No. 10/306,331 filed on Nov. 27, 2002 and U.S. Ser. No. 10/355,462 filed on Jan. 31, 2003, both of which are incorporated herein by reference in their entirety. The present application may also be related to U.S. Ser. No. 11/810,005 filed on Jun. 4, 2007, to U.S. Ser. No. 11/453,296, filed on Jun. 13, 2006, and to U.S. Ser. No. 11/332,788 filed on Jan. 12, 2006.

STATEMENT OF GOVERNMENT SUPPORT

The present invention was made with support from the United States Government under Grant number NAS7-1407 awarded by NASA. The United States Government has certain rights in the invention.

BACKGROUND

Bacterial endospores are highly resistant, thick walled structures formed by vegetative cells during a process called sporulation, and they are quite possibly the most resistant forms of life (Hindle and Hall, 1999 *Analyst*, 124, 1599-1604). They are highly resistant to radiation, chemical agents, desiccation, and other normally harmful environments (Nicholson, W. L. et al. 2000. *Microbiol Molecular Biol. Rev.*, 64, 548). Several bacterial genera are capable of producing endospores; *Bacillus* and *Clostridium* are the two most common endospore-producing genera. Within the *Bacillus* genus is the species *Bacillus anthracis* the causative agent for anthrax.

Current methods for rapidly detecting airborne bacterial spores that can carry toxins, such as those that cause anthrax, are prohibitively costly to implement and maintain. Additionally, the present monitoring methods are limited by the use of species-specific antigens and DNA probes, which would not detect a seemingly benign species that is modified to carry the anthrax toxin (Koehler, T. M. 2002. *Current Topics in Microbiology & Immunology*, 271, 143-164; Uchida, I. 1991. *J. Bacteriol.* 175, 5329-5338).

Therefore, what is needed is an automated apparatus for rapidly detecting bacterial spores that is less costly and not limited to a particular species or DNA sequence.

SUMMARY

According to a first aspect of the present disclosure, an apparatus is provided for the detection of airborne bacterial spores, wherein the apparatus comprises: an air sampler comprising an intake; a surface connectable to the air sampler suitable for spore adhesion; a thermal lysis unit for lysing the spores on the surface resulting in release of DPA; a source of lanthanide ions for providing lanthanide ions to the released DPA on the surface to form a DPA-lanthanide complex; a lifetime-gated fluorescence spectrometer having a UV source for excitation of the DPA-lanthanide complex resulting in fluorescence and subsequent detection of the fluorescence; and a computer comprising a computer program to control automation of said apparatus.

According to a second aspect of the present disclosure, a method for the apparatus as disclosed above is provided, the method comprising the steps of: (a) operating the air sampler to deposit sampled air onto the surface; (b) moving the surface from the air sampler to a position proximal to the thermal lysis unit; (c) positioning the thermal lysis unit onto the surface, thereby allowing for thermal lysis of any spores on the surface, thus releasing DPA from any lysed spores; (d) positioning the thermal lysis unit off of the surface to a position proximal to the source of lanthanide ions; (e) operating the source of lanthanide ions to provide lanthanide ions to the surface, thereby putting the lanthanide ions in contact with any DPA on the surface, resulting in said DPA-lanthanide complex; (f) moving the surface to a position away from the source of lanthanide ions to a position proximal to the spectrometer comprising a UV source; (g) operating the spectrometer to expose the surface to the UV source, thereby exciting said DPA-lanthanide complex and producing fluorescence; (h) operating the spectrometer to detect the fluorescence resulting from the excited DPA-lanthanide complex of step (g); and (i) quantifying the fluorescence intensity and/or imaging the fluorescence of step (h).

According to a third aspect of the present disclosure, a method for the apparatus as disclosed above is provided, the method comprising the steps of: (a) operating the air sampler to deposit sampled air onto the surface; (b) moving the surface from the air sampler to a position proximal to a source of lanthanide ions; (c) operating the source of lanthanide ions to provide lanthanide ions to the surface; (d) moving the surface to a position away from the source of lanthanide ions to a position proximal to the thermal lysis unit; (e) moving the thermal lysis unit onto the surface, thereby allowing for thermal lysis of any spores on the surface, thus releasing DPA from any lysed spores, and putting DPA in contact with the lanthanide ions provided to the surface in step (c) to form said DPA-lanthanide complex; (f) moving the thermal lysis unit off of the surface to a position proximal to a spectrometer comprising a UV source; (g) operating the spectrometer to expose the surface to the UV source, thereby exciting said DPA-lanthanide complex and producing fluorescence; (h) operating the spectrometer to detect the fluorescence resulting from the excited DPA-lanthanide complex of step (g); and (i) quantifying the fluorescence intensity and/or imaging the fluorescence of step (h).

One advantage of a bacterial monitor of the present disclosure, is that the chemical marker used for detection—DPA—is essential to the viability of the bacterial spore yet is present whether the spores are alive or dead. Furthermore, since approximately $10^8$ molecules of DPA are present in each bacterial spore as compared to 1 copy of DNA, expensive sample amplification schemes are not required, which significantly lowers the complexity and cost of the monitoring apparatus. Furthermore, DPA binding to terbium exhibits a million-fold greater binding constant than amino acids or nucleic acids.

Another advantage of the present disclosure is that it is not susceptible to false positives due to natural fluctuations in bacterial spore concentrations because these fluctuations occur in a concentration regime many orders of magnitude lower (natural concentrations range from 0.01-0.5 bacterial spores per liter of air) than those, for example, present during an anthrax attack (Pastuszka, J. S. et al., 2000, *Atmospheric Environment*, 34, 3833-3842).

A further advantage of the present disclosure is that unlike other fluorescence detection methods, the DPA triggered lanthanide luminescence method for bacterial spore detection is not mired by varying background fluorescence from interferents or impurities. Specifically, terbium luminescence is long lived (t~1 ms) and consequently is amenable to lifetime gating that effectively eliminates any background fluorescence. This is because terbium lifetimes are milliseconds and fluorescence lifetimes from impurities are generally on the order of nanoseconds. Thus, after excitation of the lanthanide-DPA complex with UV light (from a Xenon flash lamp, laser or UV LED), the fluorescence is not detected for several microseconds, and with the detector programmed to capture after several microseconds, the background luminescence having occurred after nanoseconds, will not interfere.

DETAILED DESCRIPTION

Rapid detection of bacterial spores of the present disclosure is based on dipicolinic acid (DPA)-triggered lanthanide ion (terbium, europium) luminescence (Hindle and Hall, 1999 *Analyst*, 124, 1599-1604). The core of bacterial spores contains up to 1 molar (M) DPA that can be released into bulk solution by lysis of the spore (Murell, 1969, *Bact. Spore* 1, 216). The released DPA binds the lanthanide ions with high affinity and triggers intense green luminescence under UV excitation.

An apparatus according to the present disclosure herein, enables for automated monitoring of aerosolized bacterial spores by implementing a lanthanide (terbium or europium ions) luminescence assay (U.S. patent application Ser. No. 10/306,331; U.S. patent application Ser. No. 10/355,462) in conjunction with a computer-operated apparatus comprising: an aerosol capture device (air sampler) (1) (FIGS. 1, 2) a surface (2) for adherence of the spores captured by the air sampler (e.g. quartz fiber tape), a thermal lysis unit (3) to induce bacterial spore lysis, a source of lanthanide ions (4) for providing terbium or europium ions to the DPA released from the lysed spores, a lifetime-gated luminescence spectrometer (5) with UV source for excitation and subsequent detection of the DPA-lanthanide complex, an alarm programmed to sound at a specific fluorescence threshold, as well as a computer programmed to control the apparatus (FIGS. 2, 3).

In one embodiment of the present disclosure, an automated apparatus is provided for the detection of airborne bacterial spores, wherein the apparatus comprises an air sampler, and a surface connectable to the air sampler suitable for capturing spores from the air.

In a second embodiment of the present disclosure, an apparatus is provided for the detection of airborne bacterial spores, wherein the apparatus comprises an air sampler, a surface connectable to the air sampler suitable for capturing spores from the air, a thermal lysis unit for lysing the spores on the surface resulting in the release of DPA, a source of lanthanide ions for providing lanthanide ions to the released DPA to form a complex, a lifetime-gated fluorescence spectrometer with a UV source for excitation of the DPA-lanthanide complex resulting in fluorescence and detection of the fluorescence, and an alarm programmed to sound at a specific fluorescence threshold.

In another embodiment, the apparatus provided in the present disclosure is an automated apparatus that does not require outside intervention apart from establishing the program parameters and fluorescence threshold. This automated apparatus further comprises a computer program as outlined in FIG. 3.

Figure 1:
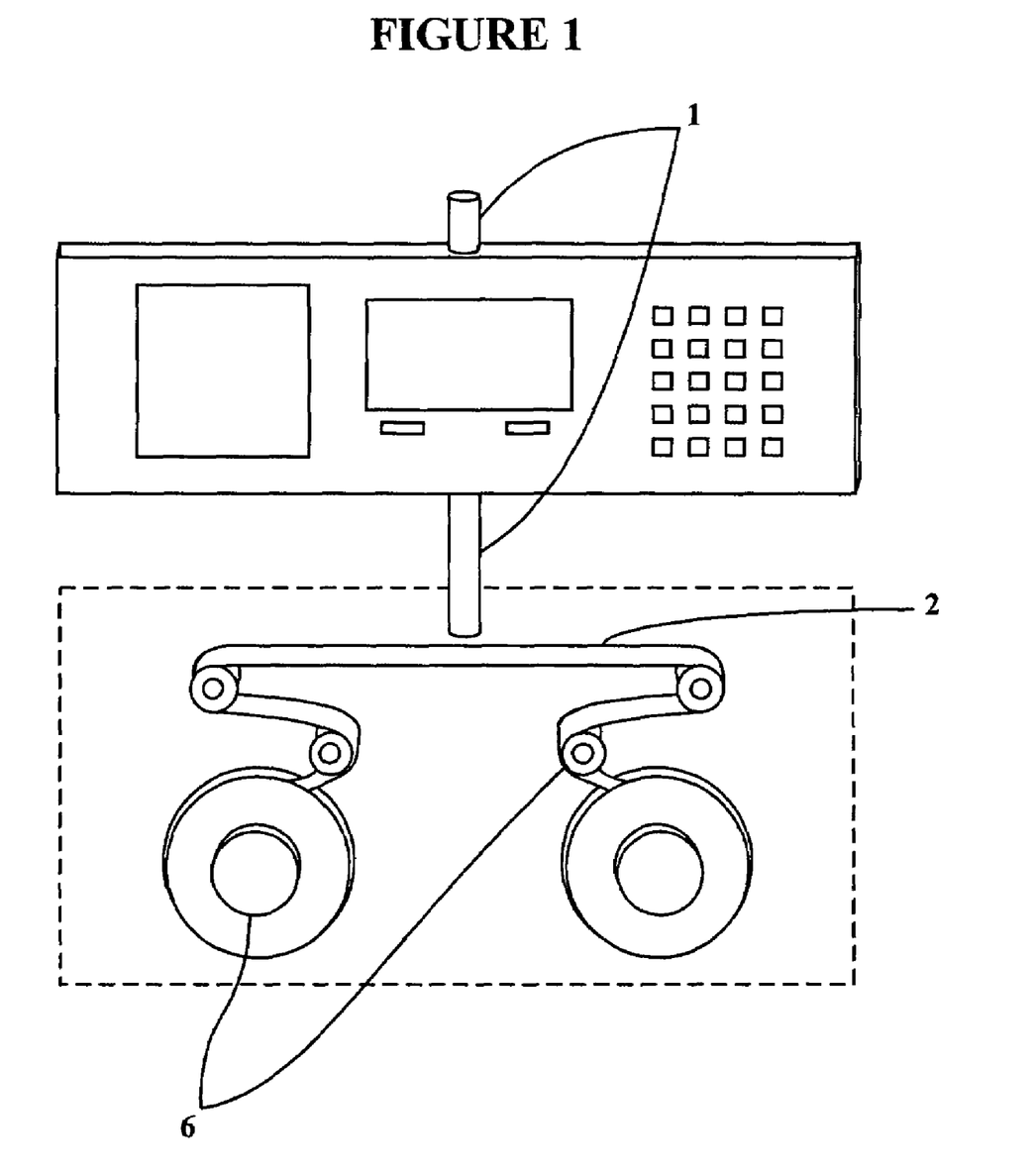
FIG. 1 shows an air sampler with quartz fiber tape on spools in accordance with a first embodiment of the present disclosure.
Figure 2:
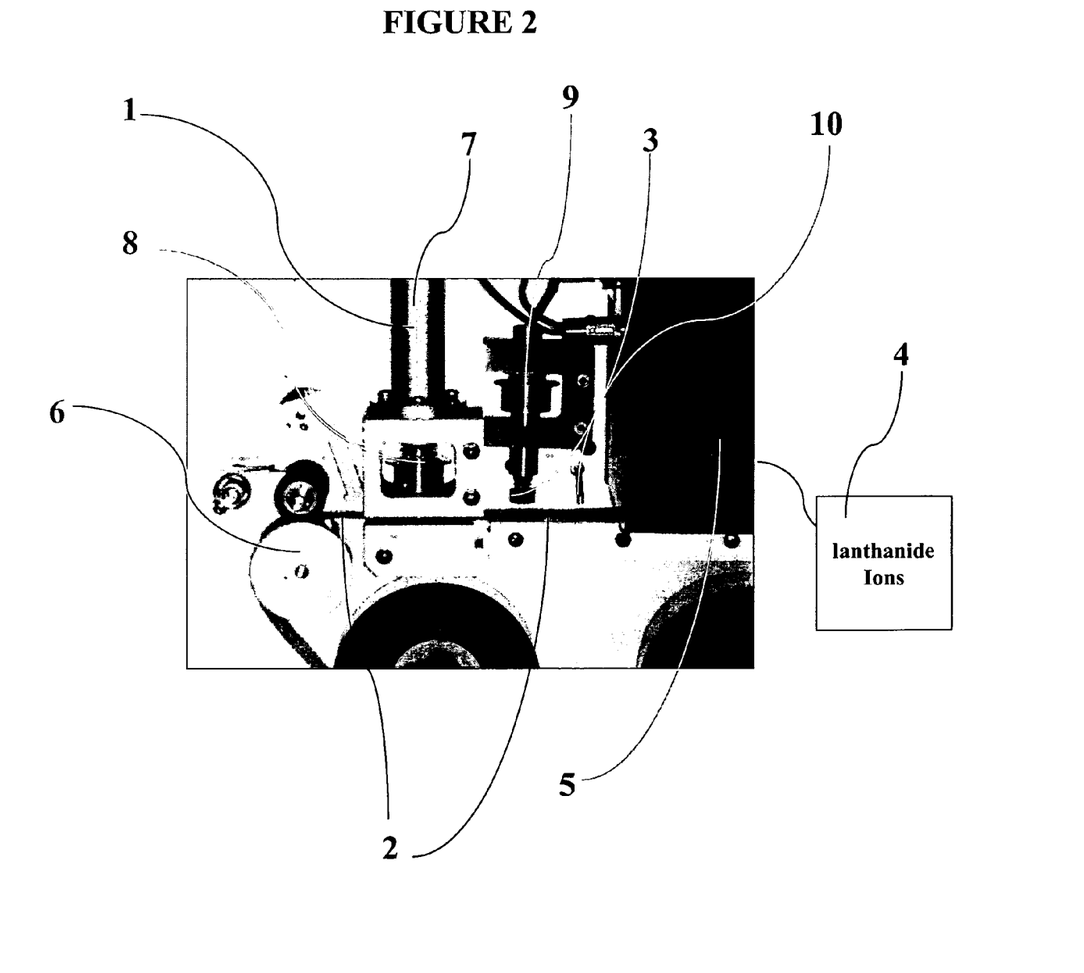
FIG. 2 shows a computer-operated, automated apparatus for the unattended monitoring of bacterial spores in accordance with a second embodiment of the present disclosure.
Figure 3:
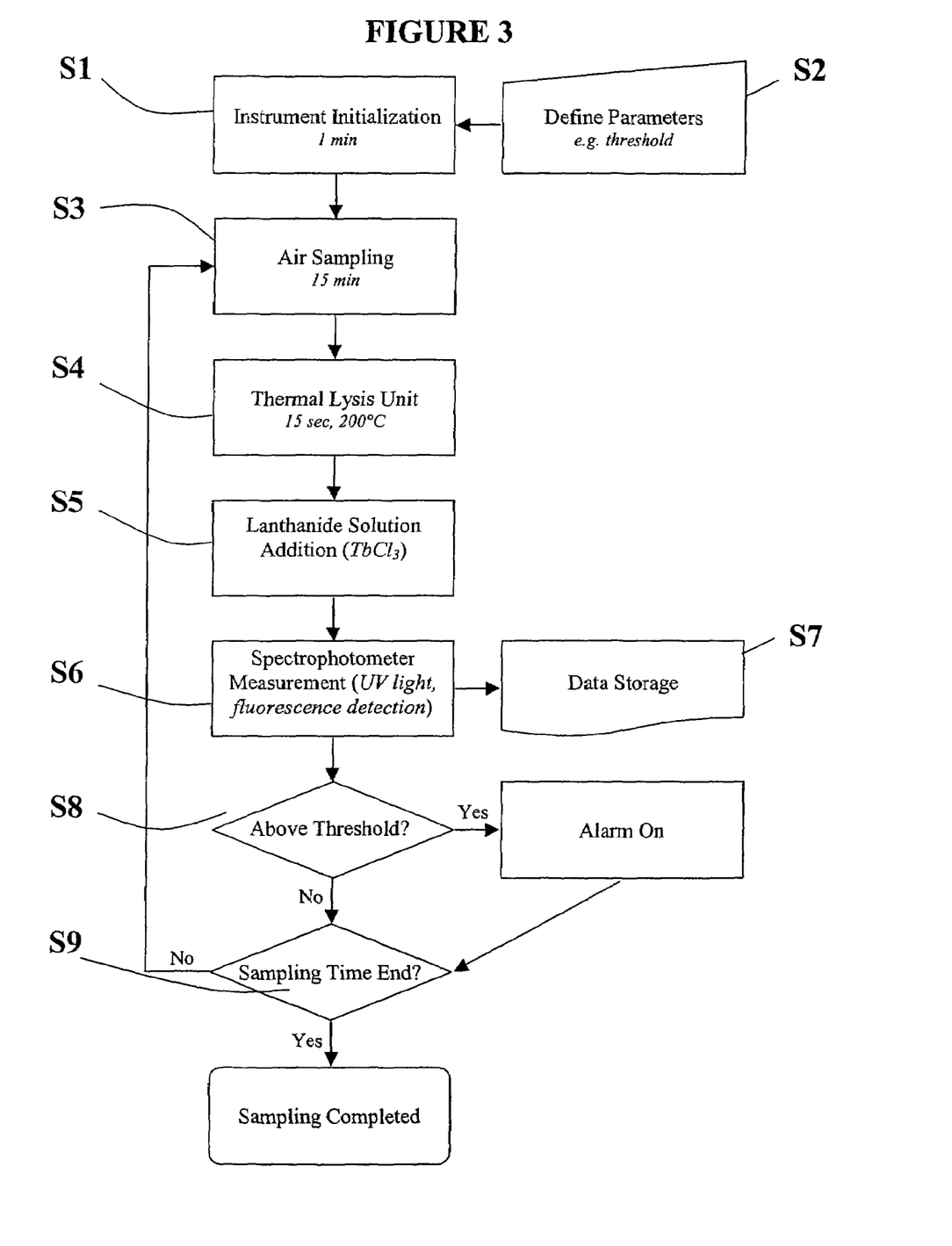
FIG. 3 shows a flow chart of steps of a computer program of the present disclosure for the automated detection of bacterial spores in the air in accordance with the present disclosure.

The air sampler (1) of the present disclosure can be of any type so long as the rate at which it samples the air (usually by way of a vacuum) is conducive to capturing spores from the air onto the surface with a high efficiency (Example 1, FIGS. 1, 2).

A surface connectable to the air sampler (2) can be of any type so long as it allows for the capture of bacterial spores from the air. Commonly this will be a type of filter tape that is directly attached to the air sampler (Example 2). Examples of surfaces for capturing the spores in the sampled air are, but are not limited to, one of the following: quartz fiber tape, electrostatically charged tape and polymer tape. The term "tape" herein refers to any surface that allows for the passage of gases in the air, and will capture microscopic species such as bacterial spores.

The glass fiber tape used in the UDT Model 7001 (Example 1, FIG. 1) allows for the option of integrating air sampling onto one spot for an extended period and/or sampling the air onto a pristine spot after a cycle of air sampling. This option is regulated by the movement of the glass fiber tape on at least two spools (6) which when stabilized, keep the tape in one place at the opposite end of the intake of the air sampler (FIG. 1).

Alternatively, after a sample of air is captured onto the tape, the tape can be moved by rotation of the spools, allowing for interaction of the tape and its contents with the thermal lysis unit. Thermal lysis is then followed by the administration of the lanthanide ions in solution, followed by excitation and finally detection.

A thermal lysis unit (3) can be of any type so long as its interaction with the surface results in the lysis of any spores on the surface (Example 3). The purpose of the thermal lysis is to release the DPA from any spores on the surface, thereby allowing for detection of the spore. Thus, thermal lysis using an easily customized lysis implement (e.g. cauterizer, soldering iron) is incorporated into the apparatus of the present disclosure for administering high temperatures (~200° C.) for the lysis of the bacterial spore(s) and subsequent release of DPA onto the surface.

A source of lanthanide ions (4) (terbium or europium) provided to the surface can be of various configurations so long as the source provides the lanthanide ions to the surface. Any lysed spores on the surface will release DPA onto the surface. The mixture of lanthanide ions and DPA molecules will form high affinity complexes on the surface that will fluoresce upon excitation by ultraviolet (UV) light (Example 4).

A lifetime-gated fluorescence spectrometer (5) with a UV source of the present disclosure (Example 5) allows for the excitation of the lanthanide-DPA complex. Accordingly, the spectrometer of the present disclosure is positioned such that the UV source (light) is directed toward the surface through which the sampled air was filtered. In this way, the UV light will be directed at any lanthanide-DPA complexes on the surface. The spectrometer of the present disclosure further contains a fluorescence spectrometer for detection of the fluorescence resulting from an excited lanthanide-DPA complex (FIG. 2).

In another embodiment, the apparatus of the present disclosure is computer-operated (FIGS. 2, 3). A computer-operated/automated apparatus comprises a computer that is programmed to control each component of the apparatus. This automated apparatus does not require outside intervention apart from establishing the program parameters and other computer input functions. This automated apparatus further comprises a computer program as outlined in FIG. 3.

For example, in an automated detector of the present disclosure, the air sampler (1) is controlled by a computer program and motorized nozzle (8) to deposit the sampled air onto a surface (2) connectable to the air sampler (S3, FIG. 3). The air sampler is further controlled with respect to the length of air sampling time. The surface for deposit of the air sample is defined as anything to which spores in the air will adhere. The surface of an automated apparatus is positioned by way of computer and motorized spools (6) that are programmed to move from a position proximal to the air sampler to a position proximal to a thermal lysis unit (3).

Movement of the thermal lysis unit is also controlled by way of a computer and motorized arm (9) allowing for the thermal lysis unit to be moved from a position proximal to the surface to a position in contact with the surface, thereby allowing for thermal lysis of any spores on the surface (S4, FIG. 3).

The temperature of the lysis unit and the length of contact with the surface are parameters of the computer program. After the lysis unit provides heat to the surface, the lysis unit is computer and motor controlled to move from the surface. Once this has occurred, by way of the computer program and motorized spools, the surface moves to a position proximal to a lanthanide source (4).

The lanthanide source contains, preferably terbium ions, but could also contain europium ions. Through the programmed commands of the computer, the lanthanide source provides the lanthanide ions (S5, FIG. 3) to the surface by way of a dropper (10). In this way, lanthanide ions are in contact with any lysed spores on the surface, which as a result of lysis, release DPA onto the surface, and allow for the formation of DPA-lanthanide complexes on the surface. After the lanthanide ions are provided to the surface, the computer program and motorized spools move the surface to a position proximal to a spectrometer (5).

The spectrometer is programmed to administer UV light via a Xenon flash lamp (laser or UV LED can also be used). This UV light exposure of the DPA-lanthanide complex excites the complex, thereby creating a fluorescence which is detected using the lifetime-gated fluorescence spectrometer, and captured as a computer image (S6, S7, FIG. 3). Such an automated apparatus as disclosed is shown in FIG. 2.

The computer is further programmed to sound an alarm if the sampled air results in a fluorescence that exceeds or meets a programmed threshold fluorescence (S2, S8, FIG. 3). A flow chart detailing the computerized functions for operating the apparatus is shown in FIG. 3.

In an additional embodiment, the apparatus of the present disclosure is programmed to continually sample air, thus the steps from air sampling to analyzing the fluorescence as disclosed can be programmed to continually repeat, or repeat for a given period of time.

In an alternative embodiment, after the surface is moved from the air sampler, the surface can be moved to a position proximal to a lanthanide source for lanthanide ions, and then subsequently moved to a position proximal to the thermal lysis unit. In other words, the thermal lysis step (S4) and the step of providing lanthanide ions (S5) can be transposed.

EXAMPLE 1

Air Sampler

For capture of aerosolized bacterial spores according to the present disclosure, a Model 7001 air sampler (Universal Detection Technology, Beverly Hills, Calif.) is shown in FIG. 1. This Model 7001 air sampler has a high transfer efficiency (>95%) for microbe-containing aerosols, and it uses a glass fiber filter tape. The air sampler shown in FIG. 2 was customized for the automated apparatus as shown. The top half of the assembly leads to the air inlet, and the bottom connects to the vacuum pump. A motorized nozzle (8) makes an airtight connection during air sampling, and is retracted after sampling to allow the tape to move forward. Similar air samplers can be used.

EXAMPLE 2

Surface for Capture of Spores

The surface (2) for capturing spores from the air sampled and taken in by the air sampler was a quartz glass fiber filter tape (Whatman) custom made for the Model 7001 air sampler (FIG. 1). Quartz fiber tape collects micron-sized particles as air is pulled through the filter. The same quartz fiber tape is used in the automated apparatus shown in FIG. 2.

EXAMPLE 3

Implement for Thermal Lysis of Spores

The thermal lysis unit (3) in FIG. 2 (consists of a soldering iron with a flat tip mounted on a motorized stage. To lyse (pop) spores the thermal lysis unit makes contact with the surface at high temps (~200° C.).

EXAMPLE 4

Source of Lanthanide Ions

The source of lanthanide ions (4) used in the present disclosure consisted of a dropper (10) providing 25 µl from a reservoir of 10-µM TbCl$_3$ (terbium chloride hexahydrate, 99.999%, Aldrich, Milwaukee, Wis.) (FIG. 2). In FIG. 2, the source of lanthanide ions is connected to the opposite surface of the apparatus, adjacent to the lanthanide ion dropper (10).

EXAMPLE 5

Lifetime-Gated Fluorescence Spectrometer

The lifetime-gated fluorescence spectrometer (5) used in the present disclosure is a miniature spectrometer with fiber-optic probe (Ocean Optics, USB2000-FL-2048-element fluorescence spectrometer and PX-2—Pulsed Xenon Flash Lamp, Dunedin Fla.). The fiber optic probe contains both fibers for excitation and detection. For background, the luminescence spectrum of 25 µl of 10-µM TbCl$_3$ on the fiber tape was subtracted from all luminescence spectra (FIG. 2).

EXAMPLE 6

Computer for Operation of Detector

The computer for operating the automated detector of the present disclosure was programmed according to the outline in FIG. 3. The computer used WINDOWS (Microsoft) and LabVIEW (National Instruments Corp.) software programs.

While several illustrative embodiments have been shown and described in the above description, numerous variations and alternative embodiments will occur to those skilled in the art. Such variations and alternative embodiments are contemplated, and can be made without departing from the scope of the invention as defined in the appended claims.

The invention claimed is:

1. An apparatus for the detection of airborne bacterial spores, wherein the apparatus comprises:
   an air sampler comprising an intake;
   a surface connectable to the air sampler, the surface suitable for spore adhesion and on-surface spore detection;
   a thermal lysis unit for lysing the spores on the surface resulting in release of dipicolinic acid (DPA);
   a source of lanthanide ions for providing lanthanide ions to the released DPA on the surface to form a DPA-lanthanide complex; and
   a lifetime-gated fluorescence spectrometer having a UV source for on-surface excitation of the DPA-lanthanide complex resulting in fluorescence and subsequent detection of the fluorescence from the surface,
   wherein the surface is connectable to the air sampler through a relative movement between the surface and the air sampler.

2. The apparatus of claim 1, wherein the air sampler is moveable between a first condition where the air sampler is proximal to the surface, and a second condition where the air sampler forms an airtight seal with the surface.

3. The apparatus of claim 1, further comprising at least two spools, the surface connectable to the intake of the air sampler being located on said spools.

4. The apparatus of claim 1, wherein the surface connectable to the air sampler is selected from the group consisting of quartz fiber tape, electrostatically charged tape and polymer tape.

5. The apparatus of claim 1, wherein the thermal lysis unit is selected from the group consisting of a cauterizer and a soldering iron.

6. The apparatus of claim 1, wherein the source of lanthanide ions comprises terbium ions.

7. The apparatus of claim 1 wherein the source of lanthanide ions comprises europium ions.

8. The apparatus of claim 1, wherein the source of lanthanide ions comprises a reservoir comprising a dropper for providing lanthanide ions to the surface.

9. The apparatus of claim 8 wherein the dropper administers 25 µl drops of 10 µM terbium chloride.

10. The apparatus of claim 1, wherein the UV source is selected from the group consisting of a Xenon flash lamp, a laser, and a UV LED.

11. A method for the operation of the apparatus of claim 1, the method comprising steps of: (a) operating the air sampler to deposit sampled air onto the surface; (b) moving the surface from the air sampler to a position proximal to the thermal lysis unit; (c) positioning the thermal lysis unit onto the surface, thereby allowing for thermal lysis of any spores on the surface, thus releasing DPA from any lysed spores; (d) positioning the thermal lysis unit off of the surface to a position proximal to the source of lanthanide ions; (e) operating the source of lanthanide ions to provide lanthanide ions to the surface, thereby putting the lanthanide ions in contact with any DPA on the surface, resulting in said DPA-lanthanide complex; (f) moving the surface to a position away from the source of lanthanide ions to a position proximal to the spectrometer comprising a UV source; (g) operating the spectrometer to expose the surface to the UV source, thereby exciting said DPA-lanthanide complex and producing fluorescence; (h) operating the spectrometer to detect the fluorescence resulting from the excited DPA-lanthanide complex of step (g); and (i) quantifying the fluorescence intensity and/or imaging the fluorescence of step (h).

12. A method for the operation of the apparatus of claim 1, the method comprising steps of: (a) operating the air sampler to deposit sampled air onto the surface; (b) moving the surface from the air sampler to a position proximal to a source of lanthanide ions; (c) operating the source of lanthanide ions to provide lanthanide ions to the surface; (d) moving the surface to a position away from the source of lanthanide ions to a position proximal to the thermal lysis unit; (e) moving the thermal lysis unit onto the surface, thereby allowing for thermal lysis of any spores on the surface, thus releasing DPA from any lysed spores, and putting DPA in contact with the lanthanide ions provided to the surface in step (c) to form said DPA-lanthanide complex; (f) moving the thermal lysis unit off of the surface to a position proximal to the spectrometer comprising a UV source; (g) operating the spectrometer to expose the surface to the UV source, thereby exciting said DPA-lanthanide complex and producing fluorescence; (h) operating the spectrometer to detect the fluorescence resulting from the excited DPA-lanthanide complex of step (g); and (i) quantifying the fluorescence intensity and/or imaging the fluorescence of step (h).

13. The apparatus of claim 1, further comprising a computer and/or an alarm programmed to sound at a specific fluorescence threshold, the computer comprising a computer program to control automation of said apparatus.

14. The apparatus of claim 1, wherein the surface connectable to the air sampler suitable for spore adhesion and on-surface spore detection is a filter tape that can be directly attached to the air sampler.

15. The apparatus of claim 1, wherein the apparatus is adapted for multiple detections each detection occurring on a different portion of the surface, through a relative movement between the surface and the air sampler.

16. The apparatus of claim 1, further comprising an arrangement for relative movement between the surface and the air sampler to adapt the apparatus to multiple detections, each detection occurring on a different portion of the surface.

17. An apparatus for the detection of airborne bacterial spores, wherein the apparatus comprises:
   an air sampler comprising an intake;
   a surface connectable to the air sampler, the surface suitable for spore adhesion and on-surface spore detection;
   a thermal lysis unit for lysing the spores on the surface resulting in release of dipicolinic acid (DPA);
   a source of lanthanide ions for providing lanthanide ions to the released DPA on the surface to form a DPA-lanthanide complex; and
   a lifetime-gated fluorescence spectrometer having a UV source for on-surface excitation of the DPA-lanthanide complex resulting in fluorescence and subsequent detection of the fluorescence from the surface,
   wherein the surface is connectable to the thermal lysis unit through a relative movement between the surface and the thermal lysis unit.

18. The apparatus of claim 17, wherein the apparatus is adapted for multiple detections each detection occurring on a different portion of the surface, through a relative movement between the surface and the thermal lysis unit.

19. The apparatus of claim 17, further comprising an arrangement for relative movement between the surface and the thermal lysis unit to adapt the apparatus to multiple detections, each detection occurring on a different portion of the surface.

20. An apparatus for the detection of airborne bacterial spores, wherein the apparatus comprises:
- an air sampler comprising an intake;
- a surface connectable to the air sampler, the surface suitable for spore adhesion and on-surface spore detection;
- a thermal lysis unit for lysing the spores on the surface resulting in release of dipicolinic acid (DPA);
- a source of lanthanide ions for providing lanthanide ions to the released DPA on the surface to form a DPA-lanthanide complex; and
- a lifetime-gated fluorescence spectrometer having a UV source for on-surface excitation of the DPA-lanthanide complex resulting in fluorescence and subsequent detection of the fluorescence from the surface,
- wherein the surface is connectable to the source of lanthanide ions or the lifetime-gated fluorescence spectrometer through a relative movement of the surface with respect to the source of lanthanide ions or the lifetime-gated fluorescence spectrometer.

21. The apparatus of claim 20, wherein the apparatus is adapted for multiple detections each detection occurring on a different portion of the surface, through a relative movement between the surface and source of lanthanide ions or the lifetime-gated fluorescence spectrometer.

22. The apparatus of claim 20, further comprising an arrangement for relative movement between the surface and the source of lanthanide ions or the lifetime-gated fluorescence spectrometer to adapt the apparatus to multiple detections, each detection occurring on a different portion of the surface.

23. A method for the operation of the apparatus of claim 13, the method comprising steps of: (a) operating the air sampler to deposit sampled air onto the surface; (b) moving the surface from the air sampler to a position proximal to the thermal lysis unit; (c) positioning the thermal lysis unit onto the surface, thereby allowing for thermal lysis of any spores on the surface, thus releasing DPA from any lysed spores; (d) positioning the thermal lysis unit off of the surface to a position proximal to the source of lanthanide ions; (e) operating the source of lanthanide ions to provide lanthanide ions to the surface, thereby putting the lanthanide ions in contact with any DPA on the surface, resulting in said DPA-lanthanide complex; (f) moving the surface to a position away from the source of lanthanide ions to a position proximal to the spectrometer comprising a UV source; (g) operating the spectrometer to expose the surface to the UV source, thereby exciting said DPA-lanthanide complex and producing fluorescence; (h) operating the spectrometer to detect the fluorescence resulting from the excited DPA-lanthanide complex of step (g); and (i) quantifying the fluorescence intensity and/or imaging the fluorescence of step (h); (j) comparing the fluorescence of step (h) with a programmed fluorescence threshold; (k) sounding the alarm if the fluorescence of step (h) exceeds and/or meets the programmed fluorescence threshold.

\* \* \* \* \*